(12) United States Patent
Alruhaimi

(10) Patent No.: US 9,622,801 B1
(45) Date of Patent: Apr. 18, 2017

(54) MANDIBULAR DISTRACTOR DEVICE

(71) Applicant: KING SAUD UNIVERSITY, Riyadh (SA)

(72) Inventor: Khalid Abdullah Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/141,773

(22) Filed: Apr. 28, 2016

(51) Int. Cl.
*A61B 17/80* (2006.01)
*A61D 1/00* (2006.01)
*A61B 17/68* (2006.01)

(52) U.S. Cl.
CPC ...... *A61B 17/8019* (2013.01); *A61B 17/8071* (2013.01); *A61D 1/00* (2013.01); *A61B 2017/681* (2013.01)

(58) Field of Classification Search
CPC ............ A61B 17/8004; A61B 17/8019; A61B 17/025
See application file for complete search history.

(56) References Cited

U.S. PATENT DOCUMENTS

| | | | |
|---|---|---|---|
| 5,769,850 A | 6/1998 | Chin | |
| 5,902,304 A | 5/1999 | Walker et al. | |
| 6,171,313 B1 | 1/2001 | Razdolsky et al. | |
| 6,355,036 B1 * | 3/2002 | Nakajima | A61B 17/66 606/54 |
| 6,673,079 B1 | 1/2004 | Kane | |
| 6,786,910 B2 | 9/2004 | Cohen et al. | |
| 9,271,780 B2 | 3/2016 | Noon et al. | |
| 2007/0162045 A1 | 7/2007 | Ahmad | |
| 2016/0058485 A1 | 3/2016 | Staehler et al. | |

OTHER PUBLICATIONS

Al-Sebaei et al., "Mandibular distraction osteogenesis: a rabbit model using a novel experimental design," *J Oral Maxillofac Surg.*, May 2005, pp. 664-672.

* cited by examiner

*Primary Examiner* — Andrew Yang
(74) *Attorney, Agent, or Firm* — Richard C. Litman

(57) ABSTRACT

A mandibular distractor device is configured for attachment to opposing sides of a mandible, e.g., a rabbit's mandible, for performing distraction osteogenesis. The distractor device includes a distractor body and an activation bar that extends through the distractor body. The activation bar can be disposed within the body such that a threaded portion of the bar is threaded to an interior wall of the anterior plate, while a smooth portion of the bar extends within the posterior plate. Once the distractor is secured to the mandible, the activation bar can be rotated incrementally to incrementally disengage the threaded portion of the activation bar from the threaded interior wall of the anterior plate. Rotation of the activation bar in this manner incrementally moves the anterior plate anteriorly within the rabbit's mouth, while the posterior plate remains in position.

4 Claims, 6 Drawing Sheets

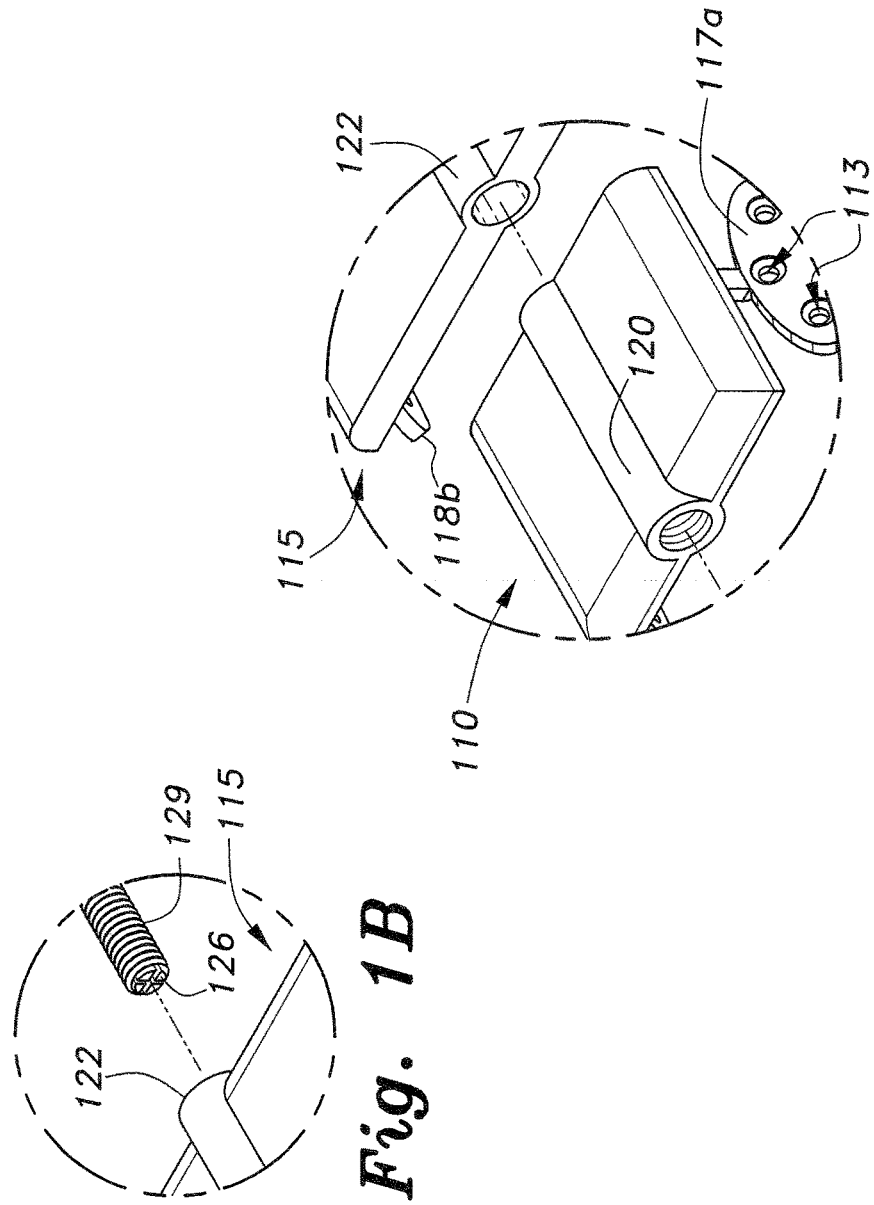

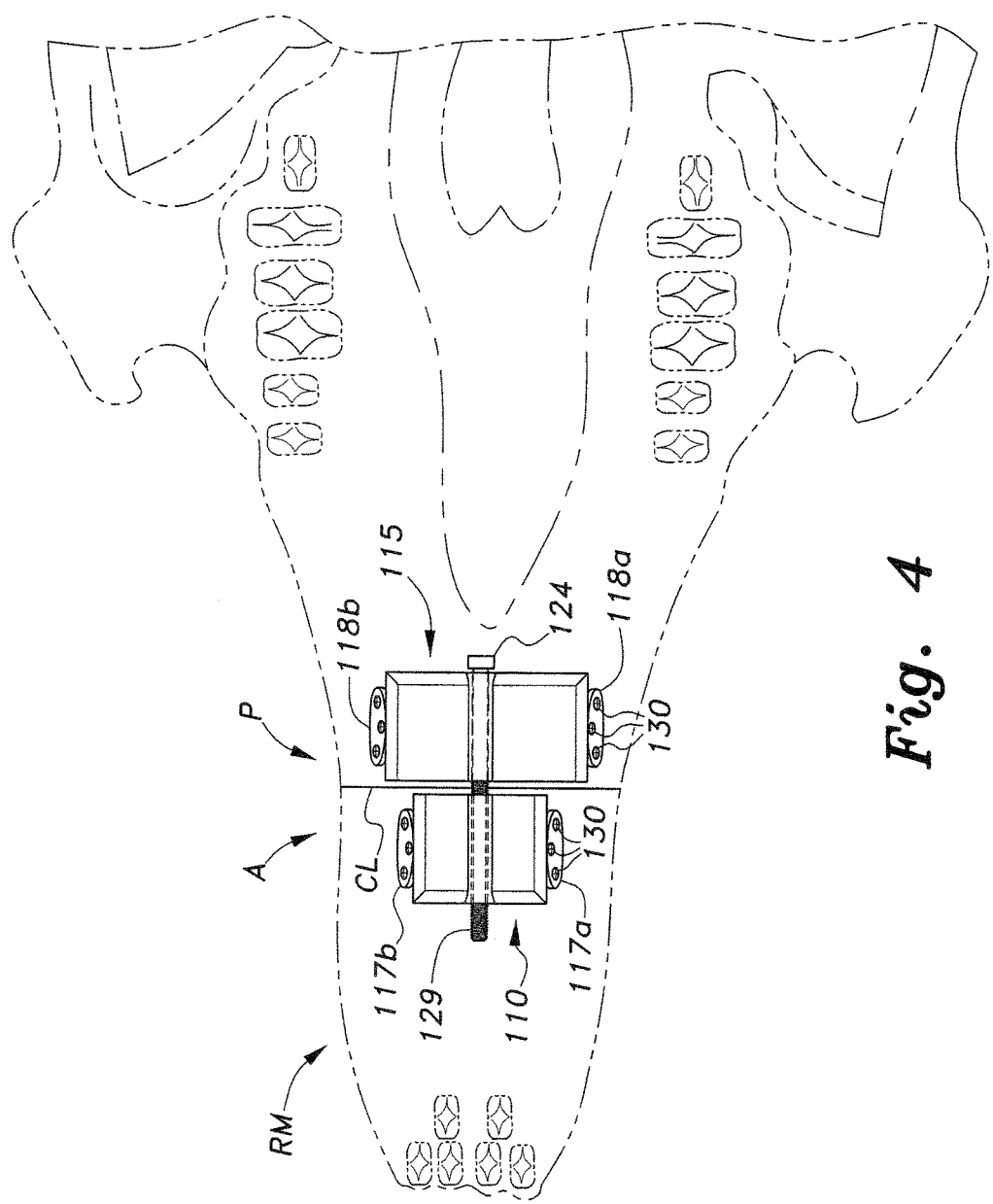

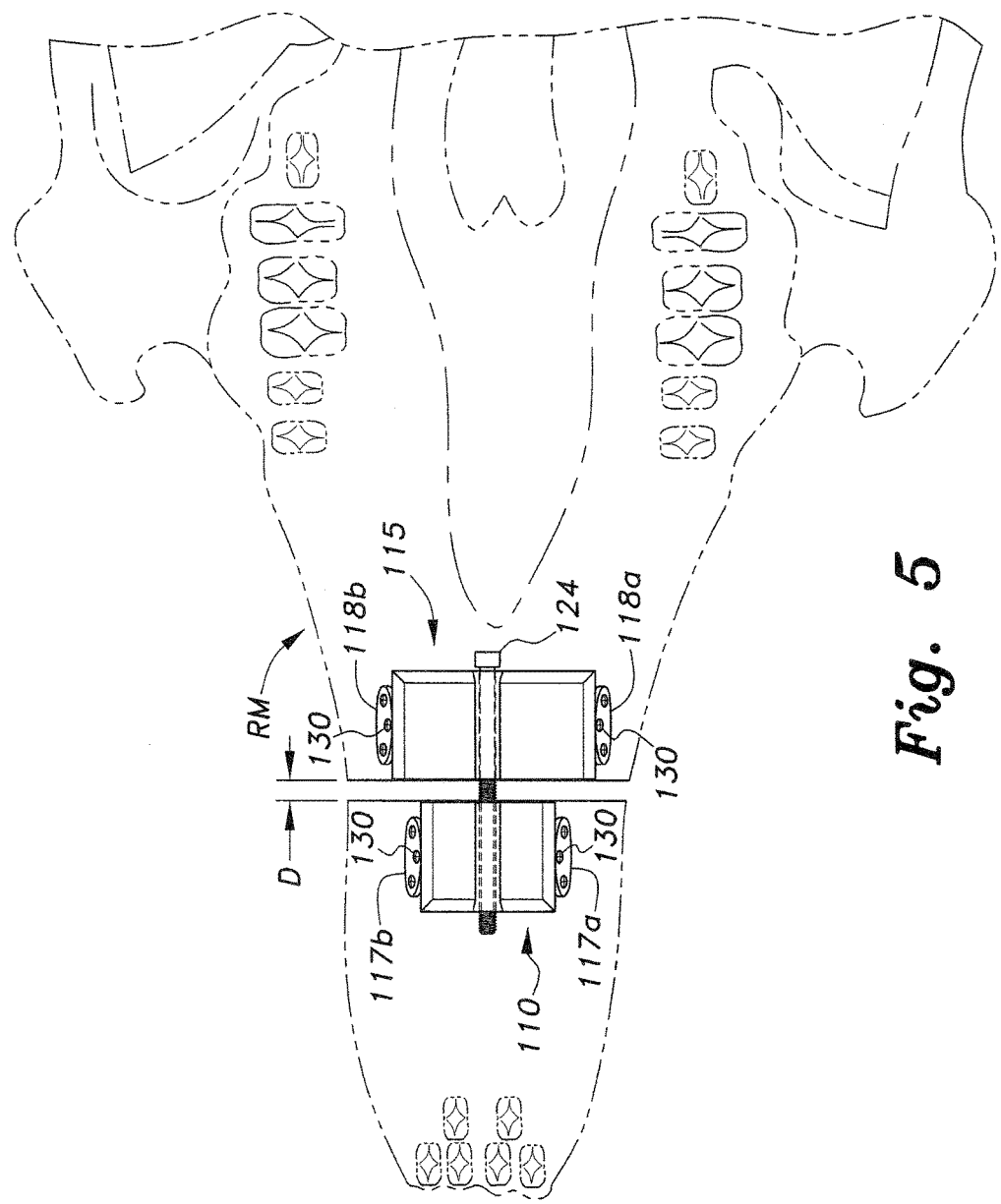

MANDIBULAR DISTRACTOR DEVICE

BACKGROUND OF THE INVENTION

1. Field of the Invention

The present invention relates to dental distractor devices, and particularly to a mandibular distractor device.

2. Description of the Related Art

Distraction osteogenesis is a process of lengthening bone in a gradual manner by distracting or separating one surgically sectioned bony part from an adjacent surgically sectioned bony part with the use of a distractor device. The distraction is typically performed in small daily increments, and generally results in the formation of new bone between the separated bony parts. The procedure is used to lengthen short bones or generate new bone in a defected or deficient bony site without the need for a bone graft.

A unilateral distraction device is generally used for distraction procedures. The unilateral device includes two separate distractors, one for each side of the mandible. Once positioned in each mandible, a portion of each distractor extends out of the patient's cheek. Subsequently, each unilateral distraction device has to be activated separately each day. The exposure of the activation bar at each side of the patient's cheek can cause discomfort and/or annoyance to the user. Further, two separate distractors involves longer surgical time and more surgical armamentarium costs.

Rabbits are typically used for experimental testing in distraction osteogenesis studies. While unilateral distraction devices (including two separate distractors) are typically used for such experiments, it is particularly difficult to affix such a distractor device directly to the lower border of a rabbit's mandible due to the divergence of the rabbit's mandible starting from the apices of the central incisors backwards, the limited thickness of the rabbit's mandible at the lower border, and the differences in the sizes of the rabbit's mandible upon variable weight and age. The divergence of the rabbit's mandible tends to restrict the possibility of affixing screws directly through the body of the distractor to the edge of the lower border of the rabbit's mandible since the screws may pass either medial or lateral to the surface of the body of the mandible which can lead to an unstable distractor.

Thus, a mandibular distractor device solving the aforementioned problems is desired.

SUMMARY OF THE INVENTION

A mandibular distractor device is configured for attachment to opposing sides of a mandible, e.g., a rabbit's mandible, for performing distraction osteogenesis. The distractor device includes a distractor body and an activation bar that extends through a central portion of the distractor body. The distractor body is defined by an anterior plate and a posterior plate, each of which are attachable to opposing sides of the mandible. The anterior plate includes a first tubular portion with a threaded interior wall. The posterior plate includes a second tubular portion with a smooth interior wall. The activation bar includes a threaded portion and a smooth portion. The activation bar can be disposed within the body such that the threaded portion of the bar is threaded to the interior wall of the anterior plate, while the smooth portion of the bar extends within the smooth interior wall of the posterior plate. The smooth portion of the bar can be spaced from the interior wall of the posterior plate to permit free rotation of the smooth portion within the posterior plate.

The device can be secured to both sides of the mandible. As such, the device can be activated for distracting both sides of the mandible at one time. To activate the device, the activation bar is rotated to unthread or disengage the activation bar from the interior wall of the anterior plate. For example, the device is rotated in daily increments to incrementally disengage the threaded portion of the activation bar from the threaded interior wall of the anterior plate. Rotation of the activation bar in this manner incrementally moves the anterior plate and the mandibular part attached thereto anteriorly within the rabbit's mouth, while the posterior plate remains in position.

These and other features of the present invention will become readily apparent upon further review of the following specification and drawings.

BRIEF DESCRIPTION OF THE DRAWINGS

FIG. 1B is an enlarged view of the anterior tip of the activation bar and the posterior end of the posterior plate of the mandibular distractor device, according to the present invention.

FIG. 1C is an enlarged view of the anterior plate of the mandibular device, according to the present invention.

FIG. 4 is a top view of a rabbit's mandible and a mandibular distractor attached thereto prior to formation of the mandibular gap, according to the present invention.

FIG. 5 is a top view of a rabbit's and the mandibular distractor attached thereto after formation of the mandibular gap, according to the present invention.

Similar reference characters denote corresponding features consistently throughout the attached drawings.

DETAILED DESCRIPTION OF THE PREFERRED EMBODIMENTS

Figure 1A:
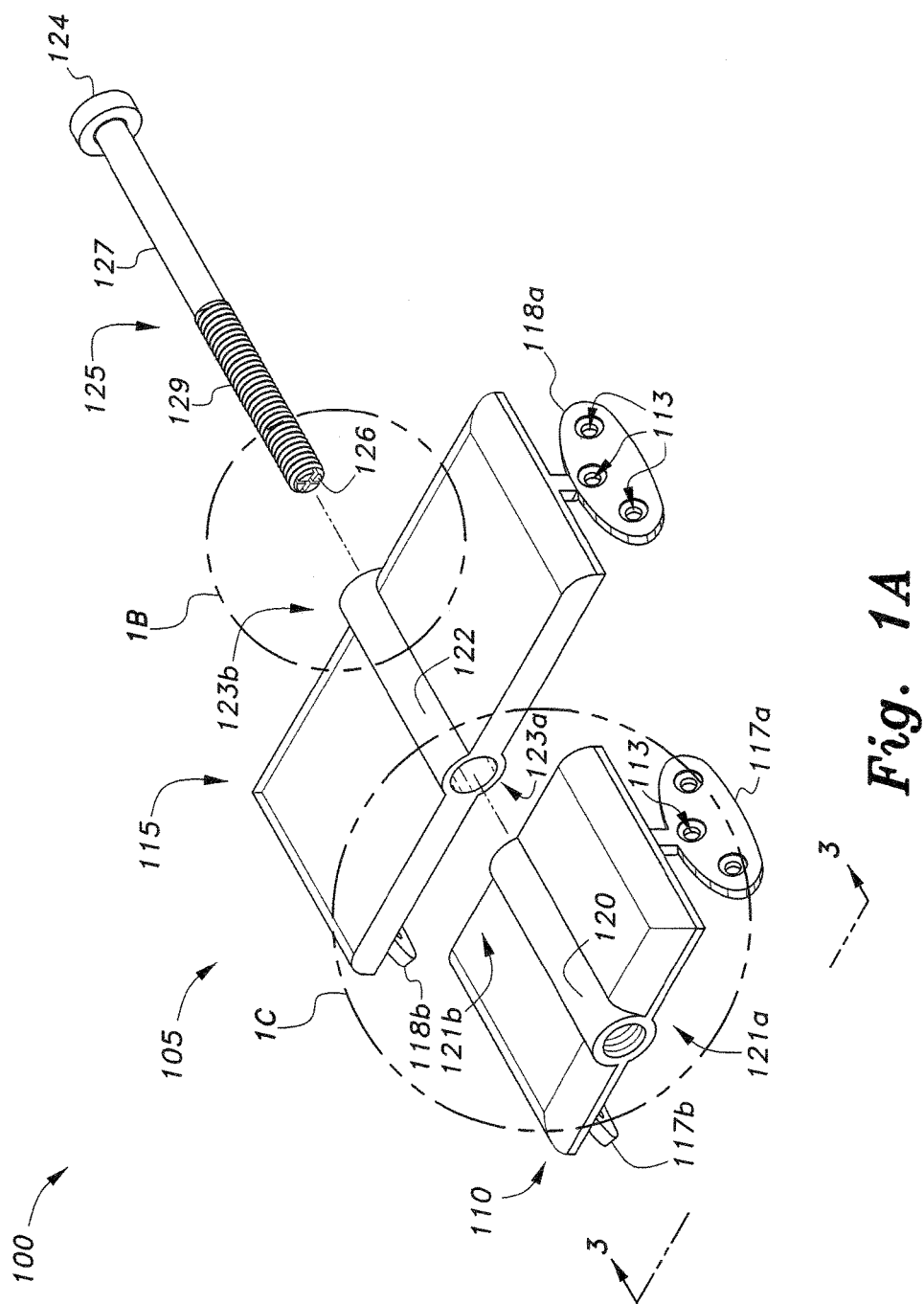
FIG. 1A is an exploded view of a mandibular distractor device, according to the present invention.

A mandibular distractor device 100 is shown in FIGS. 1A-5. According to an embodiment, the mandibular distractor device 100 is designed to attach to a rabbit's mandible RM (FIGS. 3-6), such as for experimental studies for distraction osteogenesis. The distractor device 100 includes a distractor body 105 and an activation bar 125 that extends through a central portion of the distractor body 105. The distractor body 105 is defined by an anterior plate 110 and a posterior plate 115. The anterior plate 110 includes a first tubular portion 120. The first tubular portion has an anterior end 121*a*, an opposing posterior end 121*b*, and a threaded interior wall extending between the anterior end 121*a* and the posterior end 121*b*. The posterior plate 115 includes a second tubular portion 122. The second tubular portion 122 includes an anterior end 123*a*, a posterior end 123*b*, and a smooth interior wall extending between the anterior end 123*a* and the posterior end 123*b*. The activation bar 125 includes a threaded portion 129 and a smooth portion 127.

The activation bar can be disposed within the body 105, such that the threaded portion 129 of the bar 125 is threaded to the interior wall of the first tubular portion 120 and the smooth portion 127 of the bar 125 extends within the second tubular portion 122. The smooth portion of the bar can be spaced from the interior wall of the posterior plate to permit free rotation of the smooth portion within the posterior plate.

The body 105 can be secured to both mandible sides, as described in detail below. Once the body 105 is secured to both mandible sides, the activation bar 125 can be rotated incrementally to incrementally disengage the threaded portion 129 of the activation bar 125 from the threaded interior wall of the anterior plate 110. As the activation bar 125 becomes disengaged from the anterior plate 110, the anterior plate 110 and the anterior mandibular part attached thereto move anteriorly within the rabbit's mouth and further away from the posterior plate 115 which remains in position.

Figures 2A, 2B:
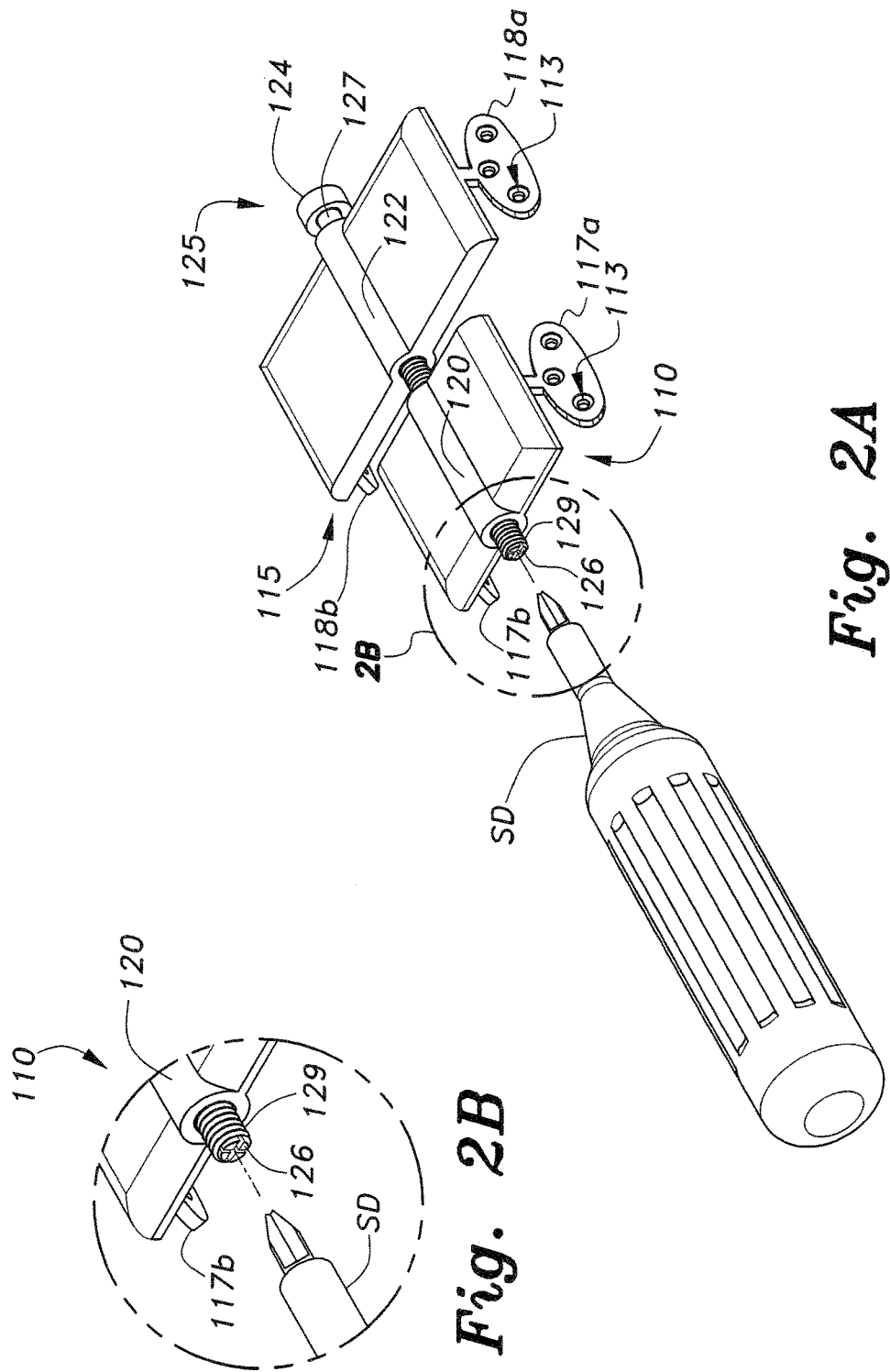
FIG. 2A illustrates the posterior plate positioned on the smooth, non-threaded portion of the activation bar and the anterior plate positioned on the threaded portion of the activation bar, according to the present invention.
FIG. 2B is an enlarged view of the anterior tip of the activation bar so, according to the present invention, illustrating how a screwdriver may be used to engage the anterior tip.

In further detail, the activation bar 125 can include a cross-shaped slot 126 that can receive a screw driver SD or other suitable instrument, as illustrated in FIGS. 1B, 2A, and 2B, to rotate the activation bar 125, e.g., clockwise, to activate the device 100, as described herein and illustrated in FIGS. 2A and 2B. The smooth, non-threaded portion 127 of the activation bar 125 includes a head portion 124 that has a diameter larger than the diameter of the activation bar 125, as illustrated in FIGS. 1A, 2A, 4, 5, and 6. The head portion 124 of the activation bar 125 is configured to prevent the posterior plate 115 of the device 100 from sliding off the activation bar 125.

The anterior plate 110 includes attachment tabs 117a and 117b at opposing sides thereof. The posterior plate 115 includes attachment tabs 118a and 118b at opposing sides thereof. Each of the attachment tabs 117a-b and 118a-b include a plurality of openings 113. Each of the plurality of openings 113 are configured to receive a fastener 130, e.g., a self-drilling screw, to secure the device to the lateral surfaces of the body of the rabbit's mandible RM, e.g., under the skin and the mucoperiosteum, and thereby affix the body 105 of the distractor to lateral surfaces on both sides of the rabbit's mandible RM. It is to be noted that the anterior plate 110 can be smaller than the posterior plate 115 to account for the divergence of the two sides of the rabbit's mandible RM, such as from the apices of the central incisors backwards. The distractor device 100, once attached to the mandible, remains within the rabbit's mouth. In other words, portions of the distractor device 100 do not protrude outside of the mouth once attached thereto, thereby minimizing discomfort to the rabbit and preventing the distractor device 100 from interfering with objects surrounding the rabbit, e.g., animal cage.

The anterior plate 110 and the posterior plate 115, as well as the activation bar 125 can be formed from any suitable type of material, such as a medical grade stainless steel material that is lightweight. The dimensions of the distractor device 100 can vary, depending upon the intended subject for which it will be used. For a rabbit, for example, the dimensions of the anterior plate 110 can be 6.0 mm long and 1.5 mm wide and the dimensions of the posterior plate 115 can be 6.0 mm long and 2.0 mm wide. Further, both portions 110, 115 can have a thickness of 2.0 mm. It is to be understood that all of the edges of the body 105 can be tapered or rounded so as to avoid, if not, substantially prevent any injury to surrounding soft-tissue. Each opening 113 can be configured to receive a 1.5 mm wide self-drilling screw. The activation bar 125 can have any suitable diameter, e.g., about 2.0 mm, and length, e.g., about 3.5 cm. The tubular portions 120, 122 can have any dimensions suitable for accommodating the activation bar 125 therein.

By way of operation, the activation bar 125 is first inserted into the posterior plate 115 of the device 100 such that the smooth portion 127 of the bar 125 is within the second tubular portion 122 and the threaded portion 129 of the bar 125 is threaded with interior wall of the first tubular portion 120. For example, the head portion 124 of the activation bar 125 can be twisted in a counterclockwise direction to engage the interior wall of the first tubular portion 120.

Figure 3:
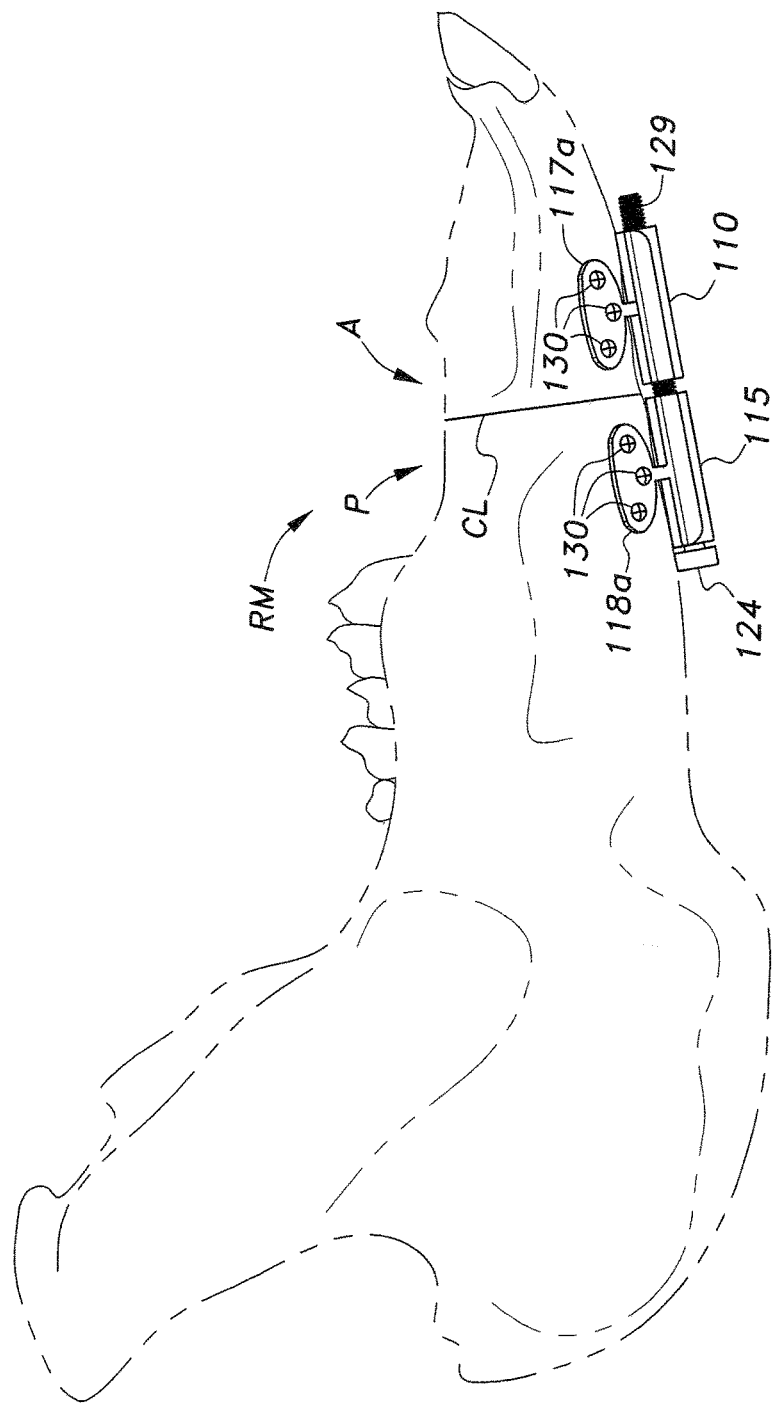
FIG. 3 is a side view of a rabbit's mandible and the mandibular distraction device attached thereto, according to the present invention.

A medical practitioner can form a corticotomy line CL on the lower border and on the lateral and medial surfaces of the rabbit's mandible RM, as illustrated in FIG. 3. The corticotomy line CL can be made posterior to the apices of the anterior incisors and anterior to the mental nerve foramen on each side of the rabbit's mandible RM. The corticotomy line CL divides the rabbit's mandible RM into two parts. The body 105 is then positioned on the lower border of the rabbit's mandible RM so that the anterior plate 110 of the device 100 is secured to one side of the corticotomy line CL and the posterior plate 115 is secured on the other side of the corticotomy line CL, as illustrated in FIG. 3. Each attachment tab is then attached within the lateral surface of each side of the rabbit's mandible RM with appropriate fasteners.

The anterior plate 110 of the body 105 can be secured to opposing sides of the anterior mandibular part A of the rabbit's mandible RM and the posterior plate 115 of the body can be secured to opposing sides of a posterior mandibular part P of the rabbit's mandible RM. Preferably, the attachment points of the device 100 are lower than the mental foramen and molar roots, as illustrated in FIG. 3. The practitioner can then separate the two sections A, P of the rabbit's mandible RM by wedging a chisel (not shown) along the corticotomy line CL. The practitioner can then utilize a screw driver SD to activate the device, i.e., rotate the activation bar 125 in a clockwise direction, and thereby move the anterior plate 110 anteriorly, as illustrated in FIG. 5. Every full rotation of the activation bar can move the anterior plate 110 (and the mandibular part attached thereto) 0.5 mm of distraction distance. It should be understood that activation of the device 100 moves the anterior plate 110 and not the posterior plate 115. In other words, the posterior plate 115 is not moved for the distraction. The daily distraction increments can be 1 mm per day, in accordance with international protocol for daily distraction, or any other suitable distance.

It is to be understood that the present invention is not limited to the embodiments described above, but encompasses any and all embodiments within the scope of the following claims.

I claim:

1. A mandibular distractor device, comprising:
a distractor body, the distractor body including an anterior plate having an anterior end, a posterior end, and a pair of opposed side edges, and a posterior plate having an anterior end, a posterior end, and a pair of opposed side edges, the anterior plate including a first tubular portion at a central portion thereof and extending substantially coplanar and coextensive to the anterior plate, wherein the remainder of the anterior plate is imperforate, the posterior plate including a second tubular portion at a central portion thereof and extending substantially coplanar and coextensive to the posterior plate, wherein the remainder of the posterior plate is imperforate, the first tubular portion including a threaded interior wall extending continuously between the anterior end and the posterior end, the second tubular portion including a smooth interior wall extending continuously between the anterior end and the posterior end, wherein the anterior plate and the posterior plate each include attachment tabs extending from the opposing sides thereof, the attachment tabs configured for attachment to lateral surfaces of a mandible; and an activation bar extending through the first and second tubular portions of the distractor body, the activation bar having an anterior terminal end and a posterior end, wherein the activation bar further includes a threaded portion contiguous to the anterior terminal end and a smooth portion contiguous to the threaded portion and extending continuously to the posterior end, the threaded portion detachably engaged to the threaded interior wall of the first tubular portion.

2. The mandibular distractor device according to claim 1, wherein the anterior plate is smaller than the posterior plate.

3. The mandibular distractor device according to claim 1, wherein the activation bar includes a head portion at one end thereof, the head portion having a diameter greater than a remainder of the activation bar.

4. The mandibular distractor device according to claim 3, wherein the activation bar includes a cross-shaped slot at an opposing end thereof.

* * * * *